United States Patent
Griinari et al.

(10) Patent No.: US 9,931,312 B2
(45) Date of Patent: *Apr. 3, 2018

(54) LIPID COMPOSITION FOR THE PREVENTION OR TREATMENT OF SKIN PROBLEMS

(71) Applicant: OLINI LTD., Espoo (FI)

(72) Inventors: Mikko Griinari, Espoo (FI); Inge Bruheim, Volda (NO)

(73) Assignee: OLINI LTD., Espoo (FI)

( * ) Notice: Subject to any disclaimer, the term of this patent is extended or adjusted under 35 U.S.C. 154(b) by 112 days.

This patent is subject to a terminal disclaimer.

(21) Appl. No.: 15/183,052

(22) Filed: Jun. 15, 2016

(65) Prior Publication Data

US 2016/0296487 A1  Oct. 13, 2016

Related U.S. Application Data

(63) Continuation of application No. 14/342,199, filed as application No. PCT/FI2012/050846 on Aug. 31, 2012, now Pat. No. 9,375,414.

(30) Foreign Application Priority Data

Sep. 2, 2011 (FI) .................................. 20115862

(51) Int. Cl.
| | | |
|---|---|---|
| *A61K 31/02* | (2006.01) | |
| *A61K 8/67* | (2006.01) | |
| *A61Q 19/00* | (2006.01) | |
| *A61K 31/202* | (2006.01) | |
| *A61K 31/201* | (2006.01) | |
| *A61K 31/355* | (2006.01) | |
| *A61K 8/36* | (2006.01) | |
| *A61Q 5/00* | (2006.01) | |
| *A61Q 19/08* | (2006.01) | |
| *A61K 36/87* | (2006.01) | |
| *A61K 36/899* | (2006.01) | |
| *A61K 36/185* | (2006.01) | |
| *A61K 36/28* | (2006.01) | |
| *A61K 36/30* | (2006.01) | |
| *A61K 36/48* | (2006.01) | |
| *A61K 36/52* | (2006.01) | |
| *A61K 36/66* | (2006.01) | |
| *A23L 33/115* | (2016.01) | |
| *A61K 9/48* | (2006.01) | |

(52) U.S. Cl.
CPC .......... *A61K 31/202* (2013.01); *A23L 33/115* (2016.08); *A61K 8/361* (2013.01); *A61K 8/678* (2013.01); *A61K 9/48* (2013.01); *A61K 31/201* (2013.01); *A61K 31/355* (2013.01); *A61K 36/185* (2013.01); *A61K 36/28* (2013.01); *A61K 36/30* (2013.01); *A61K 36/48* (2013.01); *A61K 36/52* (2013.01); *A61K 36/66* (2013.01); *A61K 36/87* (2013.01); *A61K 36/899* (2013.01); *A61Q 5/00* (2013.01); *A61Q 19/005* (2013.01); *A61Q 19/007* (2013.01); *A61Q 19/008* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

2008/0213357 A1    9/2008  Hebard

FOREIGN PATENT DOCUMENTS

WO    2010/067206    6/2010

OTHER PUBLICATIONS

International Search Report and Written Opinion, International Patent Application No. PCT/FI2012/050846, dated Nov. 22, 2012.
Brosche et al., "Effect of borage oil consumption on fatty acid metabolism, transepidermal water loss and skin parameters in elderly people", Archives of Gerontology and Geriatrics, 2000; 30(2): 139-150.
Callaway et al., "Efficacy of dietary hempseed oil in patients with atopic dermatitis", Journal of Dermatological Treatment, 2005; 16(2): 87-94.
Noli et al., "Conjugated linoleic acid and black currant seed oil in the treatment of canine atopic dermatitis: A preliminary report", Veterinary Journal, 2007; 173(2): 413-421.
Schoenherr et al., "Nutritional modification of inflammatory diseases", Clinical Techniques in Small Animal Practice, 1997; 12(3): 212-222.
Miller et al., "Dietary supplementation with ethyl ester concentrates of fish oil (n-3) and borage oil (n-6) polyunsaturated fatty acids induces epidermal generation of local putative anti-inflammatory metabolites." J. Invest. Dermatol., 1991, 96:98-103.
Ziboh and Chapkin, "Biologic significance of polyunsaturated fatty acids in the skin." Arch. Dermatol., 1987, 1-23:1686a-1690a.
Ziboh et al: "Metabolism of polyunsaturated fatty acids by skin epidermal enzymes: generation of antiinflammatory and antiproliferative metabolites." Am. J. Clin. Nutr., 2000, 71(suppl):361S-366S.

*Primary Examiner* — Jennifer A Berrios
(74) *Attorney, Agent, or Firm* — Casimir Jones S.C.

(57) ABSTRACT

The invention relates to a novel lipid composition. Further, the invention relates to the use of a lipid composition for the treatment, alleviation and prevention of skin problems.

12 Claims, 2 Drawing Sheets

LIPID COMPOSITION FOR THE PREVENTION OR TREATMENT OF SKIN PROBLEMS

CROSS-REFERENCE TO RELATED APPLICATIONS

This application is a divisional of U.S. patent application Ser. No. 14/342,199, filed Apr. 14, 2014, now allowed as U.S. Pat. No. 9,375,414, which is a Section 371 U.S. national stage entry of International Patent Application No. PCT/FI2012/050846, International Filing Date Aug. 31, 2012, which published on Mar. 7, 2013 as Publication No. WO 2013/030459, which claims the benefit of Finnish Application No. 20115862, filed Sep. 2, 2011, the contents of which are incorporated by reference in its entirety.

FIELD OF THE INVENTION

The invention relates to a lipid composition. Further, the invention relates to the use of said lipid composition for alleviating, preventing or treating skin problems.

BACKGROUND OF THE INVENTION

Skin problems are common both in humans and animals. Often the problems are due to excessive dryness of the skin. Dry skin becomes easily irritated, starts itching and becomes red. When treating sensitive and atopic skin, it is especially important to take care of the moisture balance of the skin. Upon ageing the skin becomes thinner and the maintenance of the moisture balance becomes even more challenging.

Typically, creams and emulsions, applied directly to the skin, are used to treat the excessive dryness of the skin and associated skin problems. Said treatments provide immediate relief. However, this effect does not persist for very long. It is possible to produce a more persistent moisturizing effect by providing special nourishment to the skin. In other words to supply treatment to the skin from inside. Essential fatty acids in the omega-6 and omega-3 groups of fatty acids have a central role.

Dietary strategies for improving skin condition and for prevention and treatment of skin problems as well as use to complement or replace long-term medicinal treatment have been explored. Dietary formulations based on natural oils extracted from seeds of sunflower, flax (or linseed), black currant, evening primrose, borage (or starflower), echium, hemp and sea buckthorn oil as well as fish oils, have been used as nutritional aids in the skin health area.

Fatty acids such as linoleic acid (LA), alpha-linolenic acid (ALA), gamma-linolenic acid (GLA), stearidonic acid (SDA), palmitoleic acid (POA), eicosapentaenoic acid (EPA) and docosahexaenoic acid (DHA) are components of these oils and have been identified as being important fatty acids with biological activity regarding skin health.

Linoleic acid (LA) and alpha-linolenic acid (ALA) are considered to be essential fatty acids for humans and animals, because they are not synthesized in the body and therefore are required to be obtained through the diet. Gamma-linolenic acid (GLA) and stearidonic acid (SDA) are the immediate metabolites of LA and ALA, respectively (FIG. 1).

In popular media and commercial messages involving dietary fatty acid supplements the ratio of dietary omega-6 and omega-3 groups of fatty acids of 5:1 is considered to be optimal to support various aspects of human health. Expert committees have concluded that the use of omega-6 and omega-3 ratio of 5:1 or any other ratio as guidance for nutritional adequacy is not helpful and may in fact distort the analysis of dietary fatty acid intake data [de Deckere et al. 1998]. Use of simpler ratio of LA to ALA has been recommended until more is known about the relative potencies of various n–3 fatty acid types [Anonymous 1992].

Because the enzyme that produces GLA from LA, Δ-6 desaturase, has low activity in the skin, dietary GLA is thought to be important for skin health [Ziboh and Chapkin 1987]. Combinations of dietary GLA and EPA are thought to be more effective than GLA alone with respect to skin health [Miller et al. 1991]. Thus, number of fatty acids with bioactivity towards the skin has been identified, but no consensus with respect to optimal fatty acid ratios exists.

Nutritional treatment of skin problems is the object of growing interest because of the benefits it can offer to subjects in need of said treatment. However, there are problems associated with the current lipid compositions and methods for treating skin problems.

Callaway et al. (2005) report on a clinical trial where hempseed oil was shown to be effective in alleviating some of the symptoms of atopic dermatitis at a dose of 30 mL/day. It is not clear whether the improvement in the skin condition was due to improved skin barrier function, because there was only a non-significant reduction in transepidermal water loss. The problem with the hemp seed oil supplementation is that the effective daily dose of 30 ml is fairly large and this may become a problem for some individuals not being able to ingest large amounts of oil on a daily basis.

Borage oil is a rich source of GLA and therefore it is often used alone or in combination with other natural oils in nutritional oil compositions for skin health. However, its applicability as a single oil product for skin health may be limited by its fatty acid profile consisting of high levels of omega-6 fatty acids, LA and GLA.

Natural oils are typically blended for use in nutritional oil compositions since no single fatty acid has been shown to be effective. Typically, GLA containing oils are blended with fish oil to create a mixture of omega-6 and omega-3 fatty acids that controls the inflammatory process in the skin [Ziboh et al. 2000]. The problem with fish oil containing compositions is that many people choose not to use them because of fish allergies or sensitivity to fish taste associated with the intake of fish oil containing lipid formulations (so called fishy burps).

Sea-buckthorn oil is rich in palmitoleic acid (C16:1 or POA). There is convincing evidence that sea-buckthorn oil improves the condition of mucous membranes, but the evidence that the oil or its component fatty acid, POA, has efficacy on the epidermis of the skin is less consistent [Yang and Kallio 2002].

As presented in WO 2010/067206, a composition specifically directed for use in nutrition of companion animals, has been shown to alleviate skin problems of an animal when added to the food of the companion animal. An advantage of the said lipid composition for the companion animals is the fixed ratios of the essential fatty acids (linoleic acid, LA and alpha-linolenic acid, ALA) as well as their immediate metabolites (gamma-linolenic acid GLA and stearidonic acid SDA). The disadvantage of this lipid composition for use in human subjects is the large effective dose of 20 ml/d.

There is an evident need for a low dose, well-tolerated and efficient lipid composition for treatment of skin problems.

SUMMARY OF THE INVENTION

Aspects of the invention are directed to a lipid composition. The invention is also directed to a lipid composition for use as therapeutic agent. The invention is also directed to a lipid mixture comprising the lipid composition effective on alleviating, preventing or treating skin problems in a subject in need.

The lipid composition of the present invention can be used for the improvement, prevention and treatment of skin problems, such as dryness of skin, tightness of skin, irritation of skin, reddening of skin, itching of skin, thickening of skin and exfoliation of skin or other skin problem associated with impaired skin barrier function. Further, the invention can be used for the improvement of the growth of hair and fingernails in humans or claws in animals. The invention can also be used in a method of supporting medical treatment of a skin disease. The lipid composition can be used as a dietary supplement, nutritional supplement or supplementary food.

The invention provides a low dose, well-tolerated and efficient lipid composition for treatment of skin problems.

The present invention relates to a lipid composition comprising linoleic acid (LA), alpha-linolenic acid (ALA), gamma-linolenic acid (GLA) and stearidonic acid (SDA). The lipid composition of the present invention comprises said LA and ALA in a ratio of from about 1.5:1 to about 3:1; said GLA and SDA in a ratio of from about 1.5:1 to about 3:1; said LA and GLA in a ratio of at least 1:1; and said ALA and SDA in a ratio of at least 1:1, wherein said lipid composition comprises greater than 7% or greater than about 7% (w/w) SDA and GLA in total and wherein said lipid composition comprises at least one natural tocopherol in an amount of from 0.3% (w/w) to 3% (w/w) and wherein said lipid composition is essentially free of EPA and DHA.

In some embodiments, the ratio of said LA to said ALA in said lipid compositions is about 2:1 and the ratio of said GLA to said SDA is about 2:1.

In some embodiments the lipid composition comprises said LA and ALA in a ratio of 2:1; said GLA and SDA in a ratio of 2:1, and greater than 7% (w/w) SDA and GLA in total.

In some embodiments the lipid composition comprises said LA and ALA in a ratio of 2.7:1; said GLA and SDA in a ratio of 1.6:1, and greater than 10% (w/w) SDA and GLA in total.

In some embodiments, the ratio of said LA to said GLA in said compositions is 9:1 or less and the ratio of said ALA to said SDA is 9:1 or less.

In some embodiments, the LA, said ALA, said GLA and said SDA in said compositions is obtained from evening primrose oil, echium oil and linseed oil. In some embodiments, the compositions further comprise a mixture of tocopherols. In some embodiments, the compositions are essentially free of EPA and DHA. In some embodiments, the present invention provides a lipid mixture comprising LA and ALA in a ratio of at about 2:1 and GLA and SDA in a ratio of about 2:1 effective on alleviating skin problems in humans. The lipid composition of the present invention may be applied to companion animals, such as cats and dogs.

DETAILED DESCRIPTION OF THE INVENTION

Figure 1:
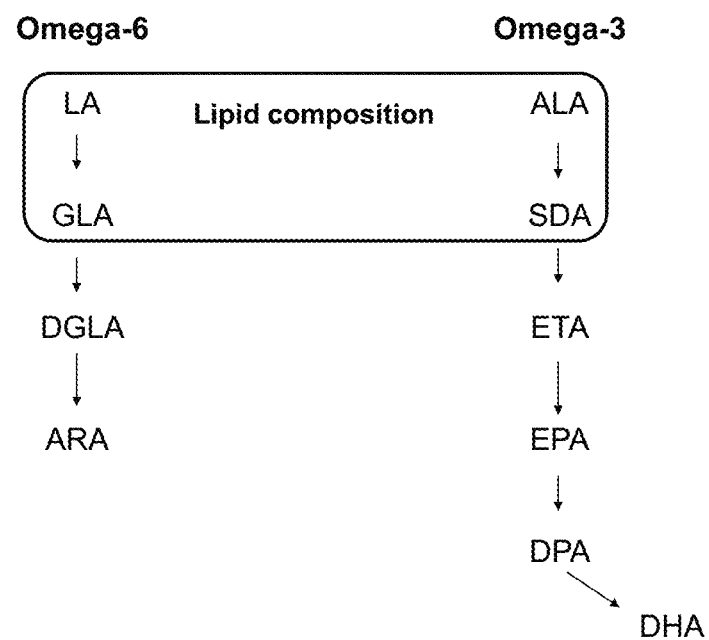
FIG. 1 illustrates the metabolism of essential fatty acids in the omega-6 and omega-3 series. Linoleic acid (LA) and alfa-linolenic acid (ALA) and their immediate metabolites, gamma-linolenic acid (GLA) and stearidonic acid (SDA), respectively are metabolized to C20 fatty acids, dihomog-amma-linolenic acid (DGLA), arachidonic acid (ARA) and eicosapentenoic acid (EPA). The box identifies the fatty acids that are present in specific ratios in the lipid composition.
Figure 2:
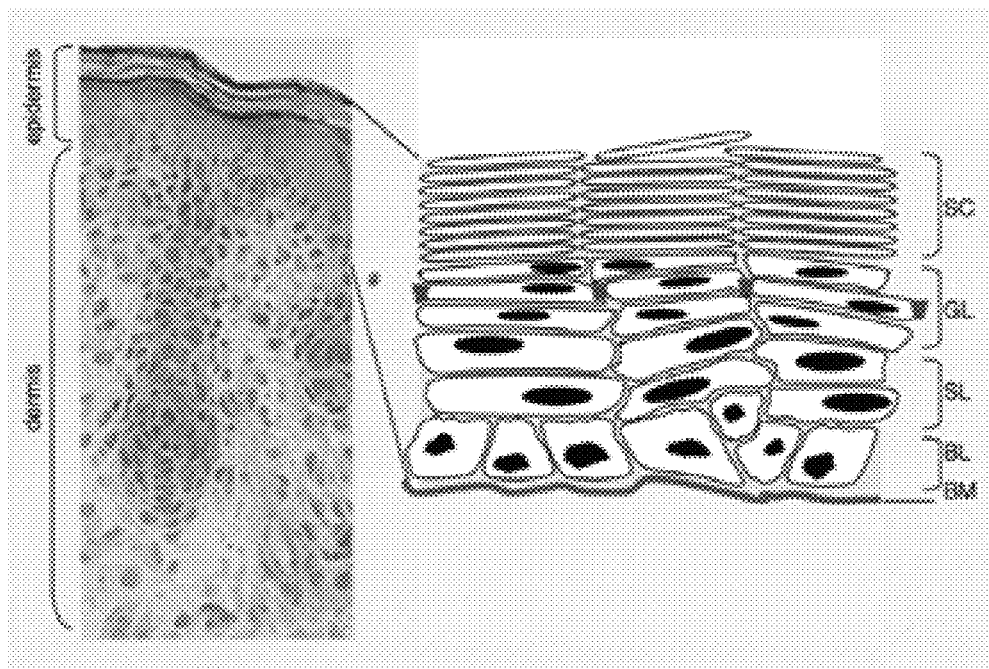
FIG. 2 illustrates structure of the skin epidermis. Abbreviations: SC=stratum corneum, GL=granular layer, SL=spinous layer, BL=basal layer.

The aim of the invention was to provide a low dose, well-tolerated and efficient lipid composition for alleviating, preventing and treating skin problems. The lipid composition of the present invention comprises a specific combination of omega-3 and omega-6 fatty acids.

As used herein, the term "omega-3 fatty acid" refers to polyunsaturated fatty acids that have the final double bond in the hydrocarbon chain between the third and fourth carbon atoms from the methyl end of the molecule. Non-limiting examples of omega-3 fatty acids include, all-cis-9,12,15-octadecatrienoic acid (alpha-linolenic acid or ALA), all-cis-5,8,11,14,17-eicosapentaenoic acid (EPA), all-cis-4,7,10,13,16,19-docosahexanoic acid (DHA) and all-cis-6,9,12,15-octadecatetraenoic acid (stearidonic acid or SDA).

As used herein, the term "omega-6 fatty acid" refers to polyunsaturated fatty acids that have the final double bond in the hydrocarbon chain between the sixth and seventh carbon atoms from the methyl end of the molecule. Non-limiting examples of omega-6 fatty acids include, all-cis-6,9,12-octadecatrienoic acid (gamma-linolenic acid or GLA) and all-cis-9,12-octadecadienoic acid (linoleic acid or LA).

The term "skin problem" refers to an impaired skin condition that is not classified as a skin disease, but can be treated, prevented or alleviated. Such impaired skin conditions include dryness and tightness of skin, irritation of skin, local reddening, thickening or itching of skin and mild exfoliation of skin. Skin problems may for example be associated to the impaired skin barrier function.

The term "skin disease" refers to a skin health condition with known clinical description, known or unknown causes, course of the disease and treatments. Such information can be found in any number of sources in the literature and on the internet.

It has been found that a novel lipid composition comprising linoleic acid (LA), alpha-linolenic acid (ALA), gamma-linolenic acid (GLA) and stearidonic acid (SDA) provides beneficial effects to subjects suffering from skin problems. The lipid composition comprises LA, ALA, GLA and SDA, wherein said LA and ALA are in a ratio of from about 1.5:1 to about 3:1; said GLA and SDA are in a ratio of from about 1.5:1 to about 3:1; said LA and GLA are in ratio of at least 1:1; and said ALA and SDA are in a ratio of at least 1:1, wherein said lipid composition comprises greater than about 7% (w/w) SDA and GLA in total and wherein said lipid composition comprises at least one tocopherol in an amount of 0.3% (w/w) to 3% (w/w) and wherein said lipid composition is essentially free of EPA and DHA. The amounts of fatty acids are given as % of total amount of fatty acids. In some embodiments, the oils have been mixed in proportions that give LA:ALA ratio of about 2:1 and the GLA:SDA ratio of about 2:1.

Furthermore, the invention discloses novel biological properties of this lipid mixture in the area of improved skin conditions in humans and animals, such as companion animals e.g. cats and dogs.

In some embodiments, the oils may also be mixed in proportions that give LA:ALA ratio less than 2:1 (e.g. 1.9:1 to 1.99:1). In some embodiments, the oil compositions have LA:ALA ratios from about 1.5:1 to about 3:1, such as 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

In some embodiments the oils may be mixed in proportions that give GLA:SDA ratio of less than 2:1 (e.g. 1.9:1 to 1.99:1). In some embodiments, the oil compositions have GLA:SDA ratios from about 1.5:1 to about 3:1, such as 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

The oil compositions of the present invention have a ratio of LA:GLA of at least 1:1, preferably up to 9:1. In some embodiments the ratio of LA to GLA may be 1:1, 2:1, 3:1, 4:1, 5:1, 6:1, 7:1, 8:1, or 9:1. The ratio of LA:GLA may be such as 3.6:1, 3.7:1, 4.6:1, 7.6:1 or 8.9:1.

The oil composition of the present invention have a ratio of ALA:SDA of at least 1:1, preferably up to 9:1. In some embodiments the ratio of ALA to said SDA may be 1:1, 2:1, 3:1, 4:1, 5:1, 6:1, 7:1, 8:1, or 9:1. The ratio of ALA:SDA may be such as 2.7:1, 3.6:1, 3.8:1, 7.6:1 or 8.8:1.

Fatty acid ratios of the lipid composition are such that the daily dose administered is small compared to the dose of the existing prior art products. The small daily dose is obtained by blending the ingredient oils in such a way that results in reduced levels of the essential fatty acids, LA and ALA, relative to their immediate metabolites, GLA and SDA in prior art products. Reduction in daily dose of the lipid composition and change in fatty acid profile cannot be achieved by concentration methods such as molecular distillation.

The lipid composition comprises in total greater than about 10% (weight-%) of SDA and GLA of total fatty acids. In some embodiments the amount of SDA and GLA in total comprises from greater than about 7%, 8%, 9%, 10%, 11% or 12%, to about 15%, 20%, 25% or 32% SDA and GLA. The amount of SDA and GLA in total may be such as 7.1%, 7.4%, 8.6%, 11.5%, 15.4%, 15.8%, 16.3%, 16.7%, or 31.5% of total fatty acids.

The amounts of fatty acids may be determined using any known analysis equipment. Non-limiting examples of such equipment are gas chromatography and HPLC.

The lipid composition of the present invention may comprise free fatty acids, or derivatives of free fatty acids such as fatty acid ethyl esters, phospholipids or other derivatives of fatty acids, oils or triglyceride mixtures of fatty acids.

In some embodiments the present invention comprises lipid compositions comprising evening primrose oil, echium oil and linseed oil. In some embodiments the oils have been mixed in proportions mentioned above. In a preferred embodiment of the invention, a mixture of evening primrose oil, echium oil and linseed oil is effective in a ratio of 58:33:7 (v/v/v). The lipid composition may comprise 58% evening primrose oil (10% GLA), 33% echium oil and 7% linseed oil.

In another preferred embodiment of the invention the lipid composition comprises 30% of concentrated evening primrose oil (20% GLA), 41.8% echium oil and 12% linseed oil. Evening primrose oil may be replaced with borage oil, such as borage oil comprising 20% GLA. The lipid composition of the present invention may further comprise safflower oil or black currant seed oil.

In another preferred embodiment of the invention the lipid composition comprises 3% safflower oil, 10% linseed oil, 42% GLA canola oil and 44% SDA soybean oil.

The lipid compositions of the present invention have novel biological properties in the area of improved skin conditions in human patients. The lipid composition of the present invention may also be administered to companion animals, such as dogs and cats.

In some embodiments the fatty acid ratios are obtained by mixing oils from different sources containing LA, ALA, GLA and SDA, such as natural oils. Non-limiting sources of these fatty acids are safflower, soybean, corn, sunflower, grape seed, poppy seed, hempseed, wheat germ, cottonseed, walnut and sesame as sources of LA; chia, kiwifruit, *perilla*, camelina and lingonberry as sources of ALA; borage (starflower) as a source of GLA and blackcurrant as a source of GLA and SDA.

The lipid composition of the present invention comprises preferably evening primrose oil, echium oil and linseed oil.

Oils with high GLA and/or SDA content are used in the present invention. Linseed oil, camelina oil, sunflower oil or safflower oil are used for balancing LA:ALA ratio, but also other oils with high LA or ALA content are useful.

In some embodiments of the present invention GLA and SDA may be obtained from genetically modified oilseed plants. Oils with enriched levels of GLA and SDA from genetically modified oil seed crops such as canola and soybean can be used in the lipid composition. Also other suitable genetically modified oilseed plants known by the skilled person in art can be used, including, but not limited to, *Arabidopsis thaliana*, rapeseed, sunflower, cotton, cocoa, peanut, safflower, coconut, flax, oil palm and corn.

Another embodiment of this invention is to include tocopherols in the oil blend. Mixed tocopherols contain four different forms of tocopherols ($\alpha, \beta, \gamma$ and $\delta$) in various ratios depending on the plant oil source from where the tocopherols are derived. Tocopherols are used in the oil blend for antioxidant protection, but they may also contribute to the observed skin health effects. Tocopherols may be included in different ratios: from relatively pure d-$\alpha$-tocopherol containing preparation such as Covitol F-1000 (Gognis, Monheim, Germany) and Novatol (Archer Daniels Midland, USA) to a preparation with a mixture of tocopherols ($\alpha, \beta, \gamma$ and $\delta$) such as Covi-Ox T70 (Cognis, Monheim, Germany) and Decanox™ (Archer Daniels Midland, USA). Tocopherols may be used in an amount of 0.3% (w/w) to 3% (w/w), preferably in an amount of 0.5%, 0.7%, 1.0%, 1.2%, 1.5%, 1.7%, 1.9%, 2.0% or 2.5%. A non-limiting example of a tocopherol is wheat germ oil tocopherol, which contains mainly $\alpha$-tocopherol. Any commercially available tocopherol mixture of natural tocopherols may be used. The amount of tocopherols refers to an absolute amount of tocopherols in the lipid composition i.e. grams of tocopherol/100 g lipid composition.

In some embodiments, the compositions of this invention are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The lipid composition may be in the form of dry powders, granules, pills, tablets, capsules, lozenges, dry products for reconstitution with water or other suitable carrier, aqueous or oily solutions or suspensions, gels, pastes, emulsions or syrups.

The composition is preferably in the form of a tablet or capsule and most preferably in the form of a soft gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Mack Publishing Co., Easton, Pa.). In other embodiments, the composition contains no traces of organic solvents which is an important property regarding the safety of consuming such compounds.

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The compositions of the present invention may also be formulated with a number of other compounds. These compounds and substances add to the palatability or sensory perception of the particles (e.g., flavorings and colorings) or improve the nutritional value of the particles (e.g., minerals, vitamins, phytonutrients, antioxidants, etc.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandrosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N-butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C-IO), ethyl acetate, ethyl butyrate, 3-methyl-3-phenyl glycidic acid ethyl ester (ethyl-methyl-phenyl-glycidate, strawberry aldehyde, C-16 aldehyde), ethyl vanillin, geraniol (3,7-dimethyl-2,6 and 3,6-octadien-1-ol), geranyl acetate (geraniol acetate), limonene (d-, 1-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum-graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Major ana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron and turmeric).

In still further embodiments, the compositions comprise at least one phytonutrient (e.g., soy isoflavonoids, oligomeric proanthcyanidins, indol-3-carbinol, sulforaphone, fibrous ligands, plant phytosterols, ferulic acid, anthocyanocides, triterpenes, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, ginkgo biloba, red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, fluorine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

The lipid composition of the present invention is useful for alleviating, preventing or treating skin problems in subjects in need. The term "subject in need" refers to humans and animals, such as companion animals. The lipid composition is suitable for use in humans. The lipid composition is also suitable for companion animals, for example dogs, cats, rabbits, gerbils, hamsters, chinchillas, fancy rats, plains viscachas and guinea pigs, and avian pets.

The lipid composition is administered to a subject in need at a dose effective in alleviating, preventing or treating skin problems. An advantage of the present invention is that the administrable dose is small allowing a convenient dosage to subjects in need. The daily dose in humans may be from 1200 mg to 5000 mg, preferably from 1700 mg to 3000 mg, such as 2450 mg. In other words the daily dose may be from 1.3 ml to 5.4 ml, preferably 2 ml to 3 ml.

The lipid composition may be used in a lipid mixture for alleviating, preventing or treating skin problems in a subject in need. The lipid composition is useful for use as a therapeutic agent.

The lipid composition is particularly useful in a method of alleviating, treating, or preventing a skin problems selected from the group consisting of: dryness of skin, tightness of skin, irritation of skin, local reddening of skin, itching of skin, thickening of skin and exfoliation of skin or other skin problem associated with impaired skin barrier function.

The term "impaired skin barrier function" refers to the reduction or weakening of the protective outer layer of the skin consisting of the dead cells of stratum corneum and the surrounding lamellar lipid layer as first described by Elias (1983).

Other examples of preferable applications of the lipid compositions of the present invention include the use for improving growth of hair and/or fingernails. Furthermore, the lipid composition according to the present invention is useful for use in a method of supporting medical treatment of a skin disease.

Non-limiting examples of skin diseases include atopic dermatitis, psoriasis, eczema or other inflammatory skin disease. Furthermore, the lipid composition may be useful in reducing risk of getting fungal, viral or bacterial infections.

In a preferred embodiment the lipid composition may be provided as a dietary supplement or nutritional supplement or supplementary food.

The present invention also relates to a method comprising administering the lipid composition to a subject in need in an amount effective for alleviating, treating, or preventing a skin problem selected from the group consisting of: dryness of skin, tightness of skin, irritation of skin, local reddening of skin, itching of skin, thickening of skin and exfoliation of skin or other skin problem associated with impaired skin barrier function, for improving growth of hair and fingernails or for use in a method of supporting medical treatment of a skin disease.

The lipid composition of the present invention is useful in strengthening the natural protective mechanism of the skin. In other words, the above mentioned skin problems associated with impaired skin barrier function may be alleviated. The present invention is based on favorable effect of the unique fatty acid ratio of the present lipid composition.

The following examples are illustrative of embodiments of the present invention, as described above, and they are not meant to limit the invention in any way.

EXAMPLES

Example 1

The lipid compositions comprising the essential fatty acid (LA:ALA) and their immediate metabolite (GLA:SDA) ratios according to the invention are produced by blending variety of natural oils containing LA, ALA, GLA and SDA. Examples of oil blends producing desired fatty acid ratios are presented in Table 1 and Table 2.

Blend A is a formulation made into a dietary supplement useful for individuals with skin problems. Blend B represents the target composition using concentrated evening primrose oil with 20% GLA available from Sanmark Ltd., Dalian, China. In Blend B borage oil (available from Sanmark Ltd., Dalian, China) containing 20% GLA may be used instead of concentrated primrose oil with 20% GLA. Blend C, D and E represent the range of compositions producing desirable fatty acid ratios by using specialty oils from GM oilseed plants [GLA canola-Liu et al. 2001; SDA soya-Lot number 070418543S Monsanto Company, St. Louis, Mo., USA]. Evening primrose oil, echium oil, linseed oil and safflower oil are provided by the manufacturer of the capsules (Aenova GmbH, Germany). Black currant seed oil is obtained from Aromtech Ltd., Tornio, Finland.

TABLE 1

Proportions of different ingredient oils (w-%) and fatty acid profiles (% of total fatty acids) in the examples of oil blends.

| | Blend A | Blend B | Blend C | Blend D | Blend E |
|---|---|---|---|---|---|
| Oils, % | | | | | |
| Evening primrose oil, 10% GLA | 58.0 | — | — | — | — |
| Evening primrose oil, 20% GLA | — | 30.0 | — | — | — |
| Safflower oil | — | 14.8 | 3.0 | 45.0 | 38.0 |
| Echium oil | 33.0 | 41.8 | — | — | — |
| Linseed oil | 7.1 | 12.0 | 10.0 | 35.0 | 30.0 |
| GLA canola oil[1] | — | — | 42.0 | 10.0 | 15.5 |
| SDA soybean oil[2] | — | — | 44.0 | 9.0 | 15.5 |
| RRR α-tocopherol | 1.9 | 1.2 | 1.0 | 1.0 | 1.0 |
| Fatty acids, % of total fatty acids | | | | | |
| 18:1 (n-9); OA | 9.3 | 10.9 | 16.6 | 15.7 | 15.8 |
| 18:2 (n-6); LA | 51.5 | 42.9 | 21.5 | 42.6 | 39.1 |
| 18:3 (n-3); ALA | 15.1 | 21.4 | 10.7 | 21.3 | 19.2 |
| 18:3 (n-6); GLA | 8.8 | 10.2 | 20.9 | 4.9 | 7.7 |
| 18:4 (n-3); SDA | 4.1 | 5.2 | 10.6 | 2.2 | 3.8 |
| GLA + SDA | 15.8 | 15.4 | 31.5 | 7.1 | 11.5 |
| LA:ALA | 2.7:1 | 2:1 | 2:1 | 2:1 | 2:1 |
| GLA:SDA | 1.6:1 | 2:1 | 2:1 | 2:1 | 2:1 |
| LA:GLA | 4.6:1 | 4:1 | 1:1 | 9:1 | 5:1 |
| ALA:SDA | 2.7:1 | 4:1 | 1:1 | 9:1 | 5:1 |
| Daily dose of oil, mg | 2450 | 2450 | 1200 | 5000 | 3000 |

[1] GLA canola - Liu et al. 2001
[2] SDA soya - Lot number 070418543S Monsanto Company, St. Louis, MO, USA

TABLE 2

Proportions of different ingredient oils (w-%) and fatty acid profiles (% of total fatty acids) in the examples of oil blends.

| | Blend F | Blend G | Blend H | Blend I |
|---|---|---|---|---|
| Oils, % | | | | |
| Safflower oil | 11.0 | 40.0 | 32.0 | 13.0 |
| Black currant seed oil | 35.0 | 28.0 | 22.0 | 35.0 |
| Echium oil | 45.0 | 9.0 | 20.0 | 32.0 |
| Evening primrose oil, 20% GLA | — | — | — | 12.5 |
| Linseed oil | 8.0 | 22.0 | 25.0 | 6.5 |
| RRR-tocopherols ($\alpha$, $\beta$, $\gamma$, $\delta$) | 1.0 | 1.0 | 1.0 | 1.0 |
| Fatty acids, % of total fatty acids | | | | |
| 18:1 (n-9); OA | 15.2 | 16.0 | 15.7 | 14.4 |
| 18:2 (n-6); LA | 35.9 | 47.6 | 42.1 | 42.2 |
| 18:3 (n-3); ALA | 23.8 | 19.1 | 23.8 | 18.8 |
| 18:3 (n-6); GLA | 10.1 | 5.4 | 5.5 | 11.3 |
| 18:4 (n-3); SDA | 6.6 | 2.0 | 3.1 | 5.0 |
| GLA + SDA | 16.7 | 7.4 | 8.6 | 16.3 |
| LA:ALA | 1.5:1 | 2.5:1 | 1.8:1 | 2.2:1 |
| GLA:SDA | 1.5:1 | 2.5:1 | 1.8:1 | 2.3:1 |
| LA:GLA | 3.6:1 | 8.9:1 | 7.6:1 | 3.7:1 |
| ALA:SDA | 3.6:1 | 8.8:1 | 7.6:1 | 3.8:1 |
| Daily dose of oil, mg | 2450 | 5000 | 4000 | 2450 |

Example 2

A two month product testing was organized in Finland during the winter months. The test involved 29 volunteers with various types of skin problems. Volunteers were recruited among individuals who reported having minor skin problems including dryness and itchiness of skin, some with excessive exfoliation and reddening of skin and some with long term skin disease such as atopic dermatitis and psoriasis. All volunteers reported frequent use of emollients and skin creams.

The test was run during the winter months because many people suffer from the consequences of dry winter air and because the drying of the skin exacerbates the existing and/underlying skin problems. Drying of the skin is associated with impairment of the skin barrier function, characteristic of the outermost layer of the skin, which is called stratum corneum (Elias 1983). Normally the skin barrier thickens when the relative humidity decreases in the environment in order to protect the skin against excessive evaporation of moisture. People with skin problems often demonstrate impaired skin barrier function and therefore suffer the consequences of moisture loss from the skin.

The product tested consisted of an encapsulated oil blend with a fatty acid composition similar to blend A presented in Table 1. Three individuals stopped the test before the test was completed—one due to dizziness, one due to urticaria suspected to be related to the test products and one due to undisclosed reasons. Of those 26 who completed the test, 18 individuals i.e. 69% reported improvement or significant improvement of their skin problem and alleviation of number of specific skin problems including reduced dryness of the skin, reduced itching, reduction in the number or complete disappearance of areas with dry, reddening and exfoliating skin. Number of individuals reporting positive effect on their skin problem also reported reduced need for use of emollients and body creams suggesting that the moisture balance of the skin improved during the test. It is also of interest to note that of those 8 individuals or 31% of individuals who completed the test reporting no effect or only minor improvement in their skin problem, 3 reported an improved condition of hair and/or fingernails.

An individual with a life-long history of atopic dermatitis reported a dramatic improvement of her skin problem. In this case, the product tested improved the condition of the atopic skin more than any previous treatment applied as adjuvant therapy (i.e. in addition to medical treatment consisting of corticosteroids). Adjuvant therapies that the individual had previously used included different topical and oral oil formulas such as those containing fish oil.

An individual with a psoriatic skin disease on continuous medication including immunosuppressant such as methotrexate reported an improved efficiency of medical treatment administered following a psoriasis flare. Typically the individual suffers excessive drying of the skin during the treatments and this condition was markedly alleviated during the period when the oil supplement was taken. It also appeared that the treatment was more effective during the period when the oil supplement was consumed. Exfoliating dry spots and crusts disappeared in some areas. In this case also, it was observed that the oil supplement can be used as an effective adjuvant treatment to the medical treatment of skin disease.

Example 3

A dietary supplementation test involving 6 volunteers was performed. Briefly, the volunteers received an oil supplement described in Table 1, Blend B for two months and were subjected to measurements of transepidermal water loss (TEWL) in the beginning and once a month during the supplementation period using VapoMeter (Delfin Technologies Ltd., Kuopio, Finland). All volunteers had reported having a dry itchy skin prior to the start of the test.

TEWL was used as an indicator of the improvement of the skin barrier function. TEWL is an established method used in studies on skin health. The method has been used for example in studies involving dietary supplementation with borage oil (Brosche and Platt 2000) and hempseed oil (Callaway et al. 2005).

The test was conducted during the midwinter period (January-March) when the relative humidity indoors is relatively constant and typically at its lowest. During this period the TEWL is reduced in individuals with normal skin barrier function but not changed or increased in individuals with impaired skin barrier function. Individuals with impaired skin barrier function typically suffer from various skin problems including dry and itchy skin during this period.

TEWL was reduced after 2 months of supplementation with the novel oil blend (Blend B, Table 1) from 18.6 g/m$^2$h to 13.1 g/m$^2$h. This reduction in TEWL reflects improved maintenance of skin moisture balance. Proportionally this reduction was almost 30% compared to the start of the test values. Volunteers also reported reduced need to use skin moisturizers due to the reduced feeling of dryness and itching of the skin.

In comparison, the proportional reduction in the skin TEWL values in subjects given borage oil (Brosche and Platt 2000) and hempseed oil (Callaway et al. 2005) were 10.8% and 21.3%, respectively. It may also be relevant to consider that the daily dose of hempseed oil was 30 ml while the dose of the novel oil blend (Blend B, Table 1) was only 2.7 ml. Thus, it is likely that the novel oil blend is more effective than known nutritional treatments in reducing transepidermal water loss in individuals predisposed to skin problems and potentially expressing impairment of skin barrier function.

Example 4

A controlled test involving 28 dogs was performed. Briefly, in this test the effects of two oil supplements were compared. One group of dogs (n=14; Group A) received an oil supplement described in Table 1, Blend A at a daily dose of 0.88 ml/10 kg body weight and the other group (n=14; Group B) received a commercial oil supplement, Nutrolin Ravintoöljy (Olini Ltd, Helsinki, Finland) the composition of which is disclosed in WO 2010/067206 (Table 10, Blend 'Typical'), at the daily dose of 4 ml/10 kg of body weight.

Dogs for the test were recruited among individuals suffering from atopic dermatitis and using a low dose of corticosteroids as a means of controlling pruritus. Dogs recruited for the test had not been given oral supplements containing essential fatty acids (LA and ALA), GLA and/or SDA at least for two months before the start of the test. Prior fish oil use was not an exclusion criteria, but dogs with possible food allergies were excluded. Dogs were kept on their usual dry dog food diets. The test period was 3 months and the response to treatments was assessed by the dog owner using on a questionnaire based on a five point scale where 1=major impairment of the skin condition, 2=minor impairment of the skin condition, 3=no change, 4=minor improvement of the skin condition and 5=major improvement in skin condition. The questionnaire was filled in once a month. Use of corticosteroids as the pruritus controlling medication was also recorded.

Two dogs from Group B stopped the test before completing the 3-month test period. One of the dogs developed an inflammatory skin condition and it had to be treated with antibiotics. The other one was removed from the study group as a result of gut obstruction. Both incidences were considered to be unrelated to treatment.

Owners of the dogs from both groups reported improvement in over 50% of dogs (8 and 7 dogs in groups A and B, respectively). No dogs were reported to have expressed a worsening of the skin condition during the 3-month test period. The average skin condition score for the whole group was 3.9 and 3.8 for Groups A and B, respectively. Use of corticosteroids varied among the individuals and there was no apparent difference between the groups. Dogs in Group A tended to show improvement in skin condition score quicker than the dogs in Group B. All dogs that improved skin condition in Group A showed improvement during month 1 and 2, while the dogs in Group B showed improvement in skin condition also during month 3.

From this test it can be seen that the novel oil blend, Blend A (Table 1), is effective at a lower dose and may act faster than Nutrolin Ravintoöljy (Olini Ltd, Helsinki, Finland; WO 2010/067206: Table 10, Blend 'Typical') in alleviating symptoms and controlling pruritus in dogs with atopic dermatitis.

Example 5

Cats are obligate carnivores and they cannot use plant based essential fatty acids efficiently. Characteristic feature of the carnivore lipid metabolism is the limited $\Delta$-6 desaturase activity. Because of this, cats do not convert LA and ALA efficiently to longer chain polyunsaturated fatty acids such as ARA and EPA (FIG. 1). We have observed that cats benefit from dietary supplementation with a lipid composition consisting of oils rich in essential fatty acids (LA and ALA) and their immediate metabolites (GLA and SDA) with respect to skin condition. After supplementing the diet of cats with the lipid composition (Blend A, Table 1) for two months a visible change in the skin condition was observed. Characteristic change was an improvement in the quality of the hair coat. Improved hair coat reflects the improved condition of the skin underneath. Dull hair coat becomes more glossy and exfoliation as well as shedding of hair is reduced. Seborrhoeic and pruritic symptoms of underlying skin problems were in some cases also reduced.

Example 6

Dietary supplement based on the composition disclosed in the present invention (see Table 1 'Blend A' for detailed composition) was produced. The product consisted of a blend of evening primrose, echium and linseed oil plus natural $\Delta$-tocopherol and the blend was put into soft gelatine capsules (VegaGels Granulat PC®, Aenova GmbH, Germany). Each capsule weighs 1306 mg with 815 mg of oil. Recommended daily dose is 3 capsules delivering total of 2445 mg of oil. Thus, daily intakes of LA, ALA, GLA and SDA are 990 mg, 368 mg, 214 mg and 135 mg. Daily intake of $\Delta$-tocopherol provided in the capsules is 46 mg.

The product is useful for individuals with skin problems including those that have dry, irritated and sensitive skin as well as for aging and atopic skin. Because the oil blend does not include any fish oil and the gelatine capsule is made from non-animal based ingredients the product is suitable for strict vegetarian consumers and for those who are allergic or do not like the taste of fish.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

REFERENCES

Anonymous, (1992). Recommendations for intakes of unsaturated fatty acids. Pp. 153-163 in Unsaturated fatty acids: Nutritional and Physiological Significance. Thereport of the British Nutrition Foundation Task Force. London: Chapman & Hall.

Brosche, T. and D. Platt (2000). Effect of borage oil consumption on fatty acid metabolism, transepidermal water loss and skin parameters in elderly people. Arch. Gerontol. Geriatr. 30(2):139-150.

Callaway, J., U., Schwab, L., Harvima, P., Halonen, O., Mykkanen, P., Hyvonen, and T. J., Jarvinen (2005). Dermatological Treatment, 16: 87-94.

de Deckere, E. A. M, Korver, O., Verschurn, P. M., and Katan, M. B. (1998). Health aspects of fish and omega-3 fatty acids from plant and marine origin. Eur. J. Clin. Nutr. 52:749-753.

Elias, P. M. (1983). Epidermal lipids, barrier function and desquamation. J. Invest. Dermatol. 80:44-49.

Liu, J.-W., S. DeMichele, M. Bergana, E. Bobik, Jr., C. Hastilow, L.-T. Chuang, P. Mukerji, and Y-S. Huang (2001). Characterization of oil exhibiting high γ-Linolenic acid from a genetically transformed canola strain JAOCS 78: 489-493.

Miller, C. C., Tang, W., Ziboh, V. A. and Fletcher, M. P. (1991). Dietary supplementation with ethyl ester concentrates of fish oil (n–3) and borage oil (n–6) polyunsaturated fatty acids induces epidermal generation of local putative anti-inflammatory metabolites. J. Invest. Dermatol. 96:98-103.

Yang, B. and H. Kallio (2002). Composition and physiological effects of sea buckthorn (Hippophae) lipids. Trends in Food Science & Technology 13:160-167.

Ziboh, V. A. and Chapkin, R. S. (1987). Biologic significance of polyunsaturated fatty acids in the skin. Arch. Dermatol. 123:1686a-1690a.

Ziboh, V. A., C. C. Miller, and Y. Cho (2000). Metabolism of polyunsaturated fatty acids by skin epidermal enzymes: generation of antiinflammatory and antiproliferative metabolites. Am. J. Clin. Nutr. 71(suppl):361S-366S.

The invention claimed is:

1. A method comprising administering a lipid formulation comprising an effective amount of linoleic acid (LA), alpha-linolenic acid (ALA), gamma-linolenic acid (GLA) and stearidonic acid (SDA), to a subject in need thereof to alleviate or treat a skin problem, wherein said formulation comprises said LA and ALA in a ratio of from about 1.5:1 to about 3:1; said GLA and SDA in a ratio of from about 1.5:1 to about 3:1; said LA and GLA in a ratio of from 1:1 to 5:1; and said ALA and SDA in a ratio of from 1:1 to 5:1, wherein said lipid formulation comprises greater than 7% w/w SDA and GLA in total, wherein said lipid formulation comprises at least one natural tocopherol in an amount of from 0.3% w/w to 3% w/w, and wherein said lipid formulation is essentially free of eicosapentaenoic acid (EPA) and docosahexaenoic acid (DHA).

2. The method of claim 1, wherein said animal is in need of treatment of a skin problem selected from the group consisting of: dryness of skin, tightness of skin, irritation of skin, local reddening of skin, itching of skin, thickening of skin, exfoliation of skin, and other skin problem associated with impaired skin barrier function; and improving growth of hair and fingernails.

3. The method of claim 1, wherein said administering alleviates a skin problem selected from the group consisting of: dryness of skin, tightness of skin, irritation of skin, local reddening of skin, itching of skin, thickening of skin, exfoliation of skin, and other skin problem associated with impaired skin barrier function; and improving growth of hair and fingernails.

4. The method of claim 1, wherein said lipid formulation comprises said LA and ALA in a ratio of 2:1; said GLA and SDA in a ratio of 2:1, and greater than 7% w/w SDA and GLA in total.

5. The method of claim 1, wherein said lipid formulation comprises said LA and ALA in a ratio of 2.7:1; said GLA and SDA in a ratio of 1.6:1, and greater than 7% w/w SDA and GLA in total.

6. The method of claim 1, wherein said lipid formulation is characterized in that said LA, said ALA, said GLA and said SDA are obtained from evening primrose oil, echium oil and linseed oil.

7. The method of claim 1, wherein said lipid formulation is characterized in that said LA, said ALA, said GLA and said SDA are obtained from natural oils selected from the group consisting of safflower, soybean, corn, sunflower, grape seed, poppy seed, hempseed, wheat germ, cottonseed, walnut, and sesame as sources of LA; from the group consisting of chia, kiwifruit, perilla, camelina, and lingonberry as sources of ALA; from starflower as a source of GLA and from blackcurrant as a source of GLA and SDA.

8. The method of claim 1, wherein said lipid formulation is characterized in that GLA and SDA are obtained from genetically modified oilseed plants.

9. The method of claim 1, wherein said lipid formulation is characterized in that the lipid composition is in the form of dry powders, granules, pills, tablets, capsules, lozenges, dry products for reconstitution with water or other suitable carrier, aqueous or oily solutions or suspensions, gels, pastes, emulsions or syrups.

10. The method of claim 1, wherein said lipid formulation is characterized in that the lipid composition is in the form of a capsule.

11. The method of claim 1, wherein said subject is a companion animal.

12. The method of claim 1, wherein said subject is a human.

* * * * *